United States Patent [19]

Harris

[11] Patent Number: 5,120,953
[45] Date of Patent: Jun. 9, 1992

[54] SCANNING CONFOCAL MICROSCOPE INCLUDING A SINGLE FIBRE FOR TRANSMITTING LIGHT TO AND RECEIVING LIGHT FROM AN OBJECT

[76] Inventor: Martin R. Harris, 9 Stud Rd., Dandenong, Victoria, Australia, 3175

[21] Appl. No.: 536,653
[22] PCT Filed: Jul. 13, 1989
[86] PCT No.: PCT/AU89/00298
  § 371 Date: Jun. 25, 1990
  § 102(e) Date: Jun. 25, 1990
[87] PCT Pub. No.: WO90/00754
  PCT Pub. Date: Jan. 25, 1990

[30] Foreign Application Priority Data
  Jul. 13, 1988 [AU] Australia .................... PI9270
  Aug. 2, 1988 [AU] Australia .................... PI9618

[51] Int. Cl.$^5$ .................................... H01J 5/16
[52] U.S. Cl. ........................ 250/227.20; 250/216
[58] Field of Search ............ 250/227.20, 227.28, 250/227.26, 560, 561, 216; 350/96.16

[56] References Cited

U.S. PATENT DOCUMENTS 4,474,431  10/1984  Bricheno .................... 350/96.16
4,500,204  2/1985   Ogura ...................... 250/227.28
4,604,520  8/1986   Pohl ........................... 250/216
4,725,727  2/1988   Harder et al. ............. 250/227.28
4,873,434  10/1989  See et al. ..................... 250/235
4,959,552  9/1990   Saffert et al. ................ 250/560

OTHER PUBLICATIONS

Electronics Letters, 16 Jan. 1986, vol. 22, No. 2, "Fibre-Optic Scanning Differential Interference Contrast Optical Microscope", Iravani, pp. 103–105.

*Primary Examiner*—David C. Nelms
*Attorney, Agent, or Firm*—Nixon & Vanderhye

[57] ABSTRACT

A scanning confocal epi-illumination microscope comprising a light source (1), which may be a laser, for supplying a light beam to a light condenser (18), which may be a lens. Condenser (18) focuses the light onto object (20) to be examined so as to illuminate a point observational field on or within the object. Reflected, fluorescent or scattered light from the illuminated point field is collected by condenser (18) and transmitted to detector (34). Scanning means (16, 17, 21, 22, 25) causes illuminated point field to move in scanning pattern relative to object (20). The outgoing light passing from light source (1) to condenser (18) and the returning light are transmitted via optical fibres and a light separator to divert the return light to detector (34).

22 Claims, 12 Drawing Sheets

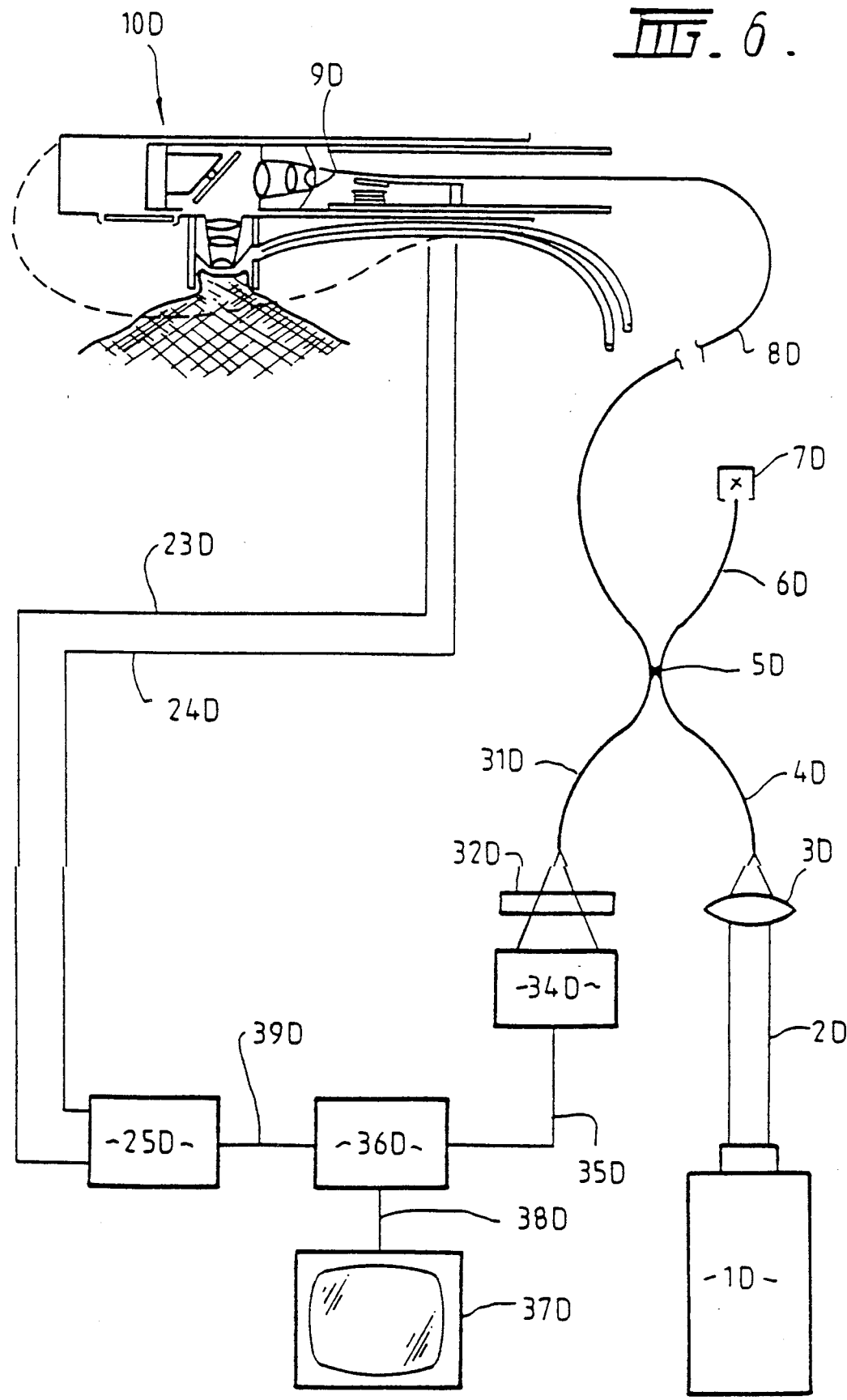

SCANNING CONFOCAL MICROSCOPE INCLUDING A SINGLE FIBRE FOR TRANSMITTING LIGHT TO AND RECEIVING LIGHT FROM AN OBJECT

TECHNICAL FIELD

This invention relates to the field of microscopy and more particularly to scanning confocal microscopes.

BACKGROUND AND SUMMARY OF THE INVENTION

The principles of a scanning confocal microscope are disclosed in U.S. Pat. No. 3,013,467 of Marvin Minsky. The basic principle is that illumination of the specimen or object to be observed is confined to a single point observational field and observation or detection is confined to that illuminated point field. A complete image is derived by scanning the specimen or object under observation point by point through a complete field of view of the microscope.

In early confocal microscopes, including that proposed in the Minsky patent, the optical system remained fixed and scanning was achieved by moving the specimen or object to be observed in a scanning pattern across the focal point of illumination. More recent high speed scanning microscopes have employed beam scanning techniques rather than movement of the specimen. Commonly, these microscopes use a laser as the high illumination light source and have a computer or video system to process and store or display the detected image signals.

Confocal microscopes have better resolution than conventional microscopes and sharper definition in that out of focus signals and interference are much reduced. They have found particular application in the examination of biological specimens by epi-fluorescence where the reduction of out of focus interference is a major advantage.

It is known to produce a confocal microscope by attaching a confocal imaging system to a conventional microscope which provides the condenser or focusing lens for the system. In all known confocal equipment, however, the light condenser the light source and the detector and all of the components defining the optical path for the microscope must be accurately positioned relative to one another and they are therefore all mounted on a bulky common body structure. The present invention provides a modified construction by which some of these components can be positioned completely independently in space without the normal rigid geometric constraints of relative location and orientation. In particular, it enables the light source and the photo-detector to be located in any desired position and without the need for a rigid mechanical connection between them and the remainder of the equipment. Other advantages of the construction provided by the invention will be apparent from the ensuing description.

DISCLOSURE OF THE INVENTION

According to the invention there is provided a scanning confocal epi-illumination microscope comprising:
a light source for supply of a light beam;
a light condenser for condensing light from said beam onto an object to illuminate a point observational field on or within the object and for receiving light emanating from that point observational field on or within the object;
a detector for detecting object emanated light received by the light condenser;
optical transmission means for transmitting the light beam from the light source to the condenser and for transmitting the object emanated light received by the light condenser to the detector; and
scanning means operable to cause relative movement between the object and the point observational field such that the point observational field traverses the object in a scanning pattern;
said optical transmission means comprising flexible optical transmitter means for transmitting the light beam between the light source and the condenser and light separator means to separate the object emanated light from the light beam.

The flexible optical transmitter means may comprise a first optical fibre extending from the light source to the light separator means and a second optical fibre extending from the light separator means to the detector. The light separator means may then comprise an optical fibre coupler coupling said first and second fibres to a third optical fibre providing an optical path for transmission of the light beam from the light source to the condenser and transmission of object emanated light from the condenser to the coupler. In this case, the scanning means may operate to move the light beam transmitted from the third optical fibre to the condenser. The scanning means may, for example, provide an optical path for the light beam from the third optical fibre to the condenser and comprise a transmission element movable to cause the scanning movement of the light beam. Alternatively, the scanning means may be operable to move the third optical fibre so as to move the beam transmitted thereby to the condenser whereby to produce said scanning movement of the light beam.

In an alternative arrangement, the light separator means may comprise a beam splitter interposed between the light source and the flexible optical transmitter means or between the flexible optical transmitter and the light condenser.

The use of the flexible optical transmitter means (usually optical fibres) enables the light source (usually a laser) and the detector to be located remotely from the remainder of the apparatus without a rigid mechanical connection to it. This attribute of the apparatus has two important consequences. Firstly, it enables production of equipment which can be added on to a conventional microscope using standard microscope optics and mechanical adjustments to produce a confocal imaging system in which the laser generator and detector can be located well away from the microscope. Secondly, it enables design of a confocal imaging system using a very compact remote head piece which can be adapted to specific purposes such as for use as an endoscope or implantable remote head microscope for medical applications.

In order that the invention and its various applications may be more fully explained, several specific embodiments will be described in some detail with reference to the accompanying drawings.

BRIEF DESCRIPTION OF DRAWINGS

FIGS. 6, 7 and 8 illustrate a modified confocal microscope system which employs a small size remote head adapted for particular use as an endoscope;

BEST MODES OF CARRYING OUT THE INVENTION

Figure 1:
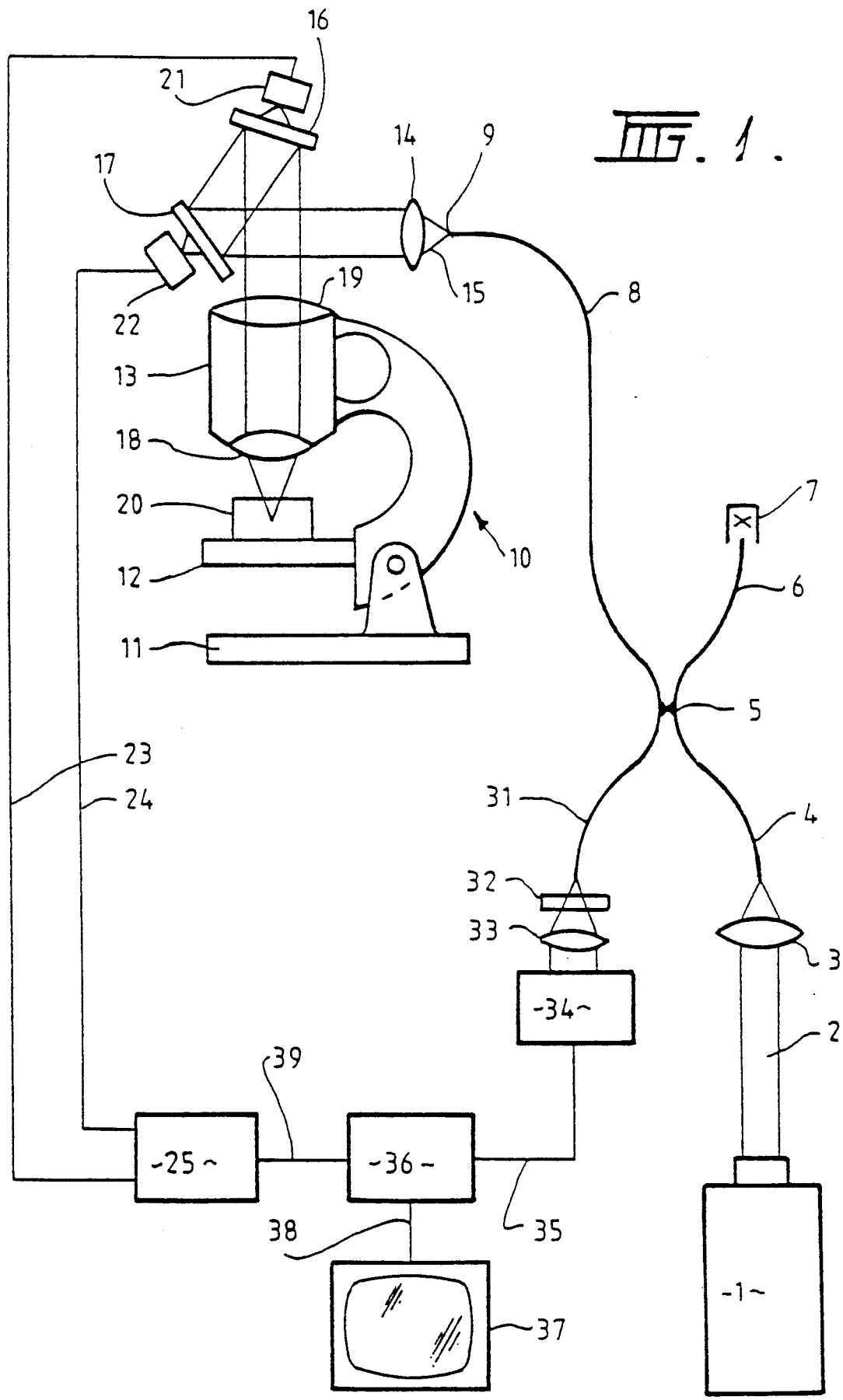
FIG. 1 illustrates one form of confocal microscope system constructed in accordance with the present invention in which separation between outgoing and return light is achieved by a fibre optic directional coupler.

FIG. 1 illustrates a scanning confocal epi-illumination microscope system in accordance with the invention. This system comprises a high intensity light source in the form of a laser generator 1 to supply a light beam 2 which is focused by a lens 3 into one end of a flexible optical fibre 4. The other end of optical fibre 4 runs into one side of a directional coupler 5 which may be a fused biconical taper coupler or other coupler for separating light rays travelling in opposite directions. The light going into one of the outgoing limbs 6 at the other side of the coupler is absorbed with minimum Fresnel reflection by an indexing matching media body 7 while light going into the other leg of the coupler at that side is transmitted by flexible optical fibre 8 from the end 9 of which it is transmitted to the optical train of an optical microscope denoted generally as 10.

Optical microscope 10 comprises a base 11 on which there is mounted a mechanically adjustable specimen support platform 12 and a microscope body 13 housing the components defining the optical train of the microscope. These optical components comprise a lens 14 to receive the light 15 diverging from the end 9 of fibre 8, a pair of mirrors 16, 17 by which the light transmitted through lens 14 is successively reflected via a beam converging lens 19 to a light condenser in the form of a lens 18 which condenses or focuses the light onto a spot or point observational field in a specimen 20 supported on the platform 12.

Mirrors 16, 17 can be moved by transducers 21, 22 in response to signals supplied through electrical connections 23, 24 from an electronic scanning signal generator 25 such that the reflected light beam is moved in X and Y directions to cause the illuminated spot to traverse the specimen in a scanning pattern. Scanning means of this kind is used in conventional scanning confocal microscopes.

As well as focusing high intensity light onto the specimen to produce an illuminated spot, the condenser lens 18 also receives light emanating from the specimen which is transmitted back through the optical train of the microscope 10 to the optical fibre 8. Depending on the nature of the specimen, this light emanating from the specimen may comprise reflected light, Raman scattered light or fluorescent light. It is to be understood that the term "emanating" as used in this specification is to be construed in a broad sense as covering any light transmitted back from the object through the condenser. This light reconverges to a focus back at the tip 9 of optical fibre 8 and travels back up that fibre to the coupler 5 where a portion of that light is transmitted via the fourth leg of the coupler and a further flexible optical fibre 31 then via a filter 32 and lens 33 to a photo-detector 34. The signal from photo-detector 34 passes through an electrical connection 35 to the signal processor 36 of a video display system which produces an image on a display screen 37. The signal from photo-detector 34 modulates the intensity of the image signal transmitted from the processing circuit 36 through output line 38 to the display screen 37 and the mechanical scanning movements of the mirrors 16, 17 are synchronized with the electronic raster scanning movements of the display system through an interconnection 39 between the electronic scanning signal generator 25 and the signal processing means 36 of the video display unit 37.

Figure 2:
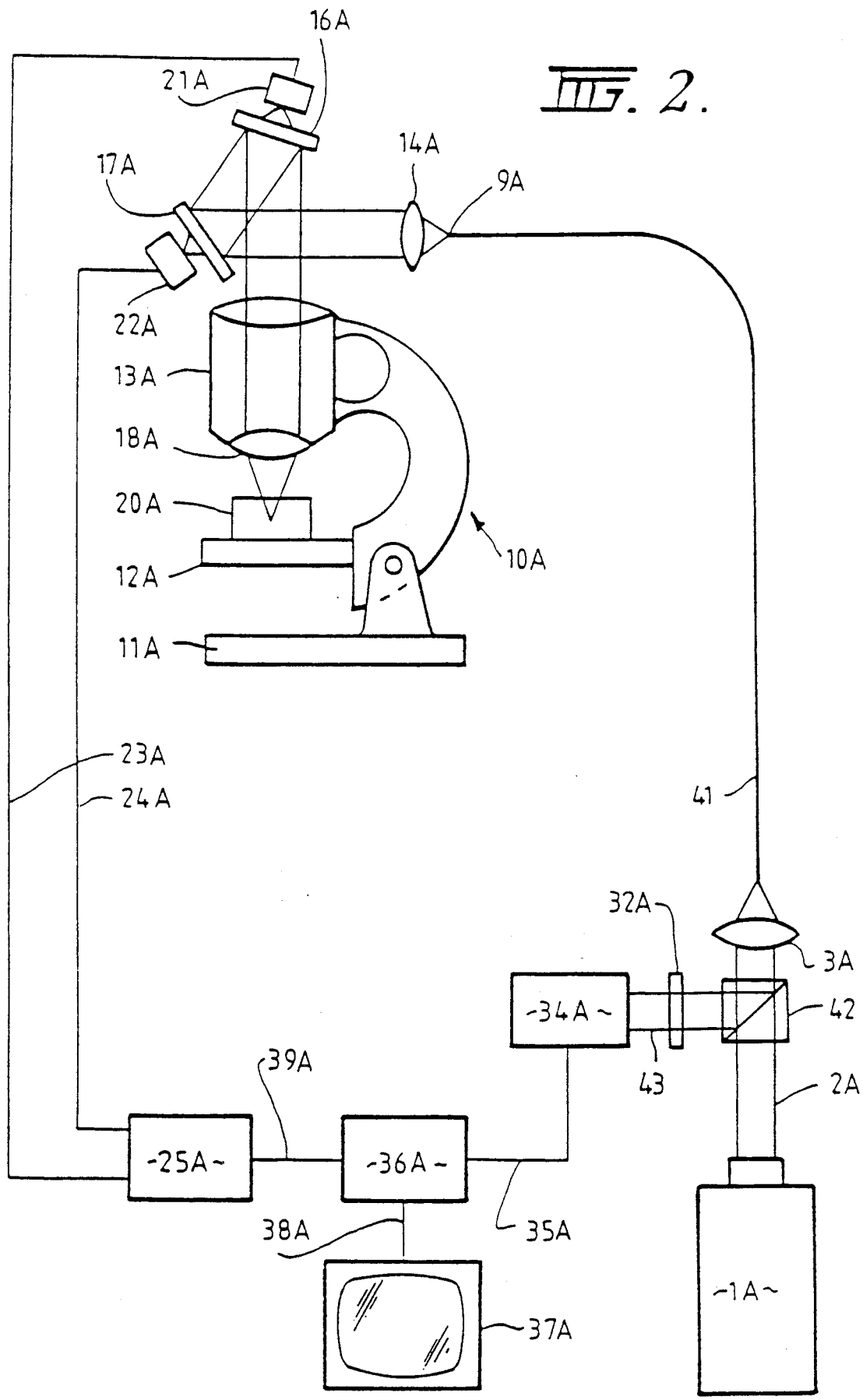
FIG. 2 illustrates a modified microscope system in which light separation is achieved by a beam splitter located between the light source and the flexible optical transmitter means of the system.

FIG. 2 illustrates a modified scanning confocal epi-illumination microscope system also constructed in accordance with the invention. This system is similar to that illustrated in FIG. 1 but it employs a beam splitter as the means for separating the returning light from the outgoing light instead of the fused bi-conical taper coupler of the apparatus in FIG. 1. Many of the components of the apparatus are identical to those of the system illustrated in FIG. 1 and operate in the same manner. These components have been identified by the same reference numerals with the addition of the post script A. In this case, the fused bi-conical taper coupler and the associated multiple optical fibres are replaced by a single optical fibre 41 onto one end of which light from the laser 1A is focused by the lens 3A and from the other end of which the light diverges to the lens 14A of microscope head 10A to traverse the optical path in the head of the microscope and illuminate the specimen as described previously with reference to FIG. 1. The returning light captured by the condenser 18A of the microscope head returns back through the same optical path and via fibre 41 to the lens' 3A. This return light is separated by means of a beam splitter cube 42 interposed between the laser source 1A and the lens 3A and which diverts the returning light in a beam 43 detected by the photo-detector 34A.

Figure 3:
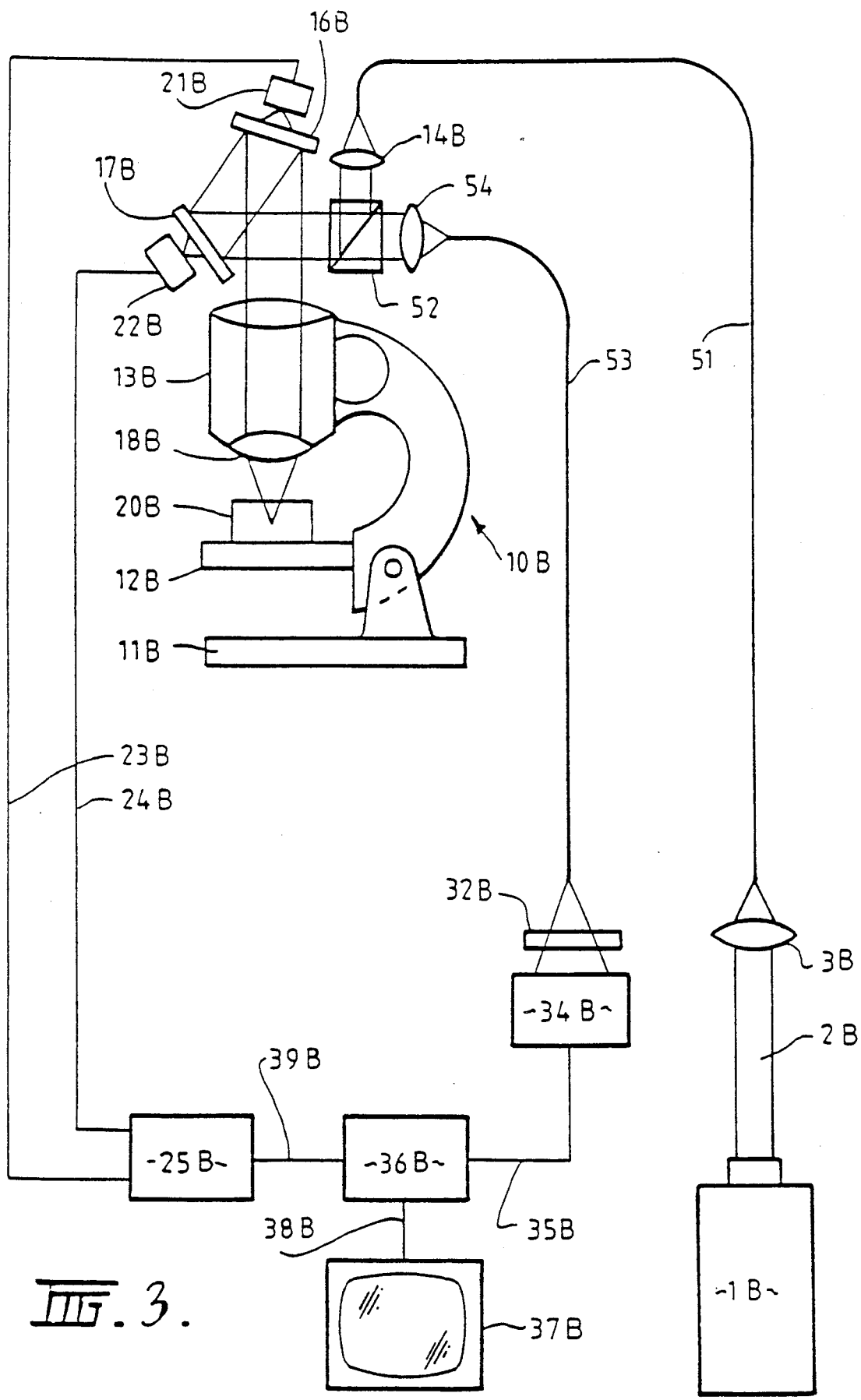
FIG. 3 is a further modified system in which light separation is achieved by a beam splitter located between the flexible optical transmitter means and the light condenser of the system.

FIG. 3 illustrates an alternative modified system in accordance with the invention in which the returning light is separated by means of a beam splitter disposed within the microscope head itself. Again, components equivalent to those of the system illustrated in FIG. 1 are identified by the same reference numerals but this time with the addition of the post script B. In this apparatus, light from the laser source 1B is focused by the lens 3B onto one end of an optical fibre 51 which transmits the light to the microscope head 10B where it is transmitted through the optical train of the microscope head to focus on a spot on the specimen to be examined. Light emanating from the same spot on the specimen is captured by the condenser 18B of the microscope head and is transmitted back through the optical train of the microscope. In this case, the microscope head is modified by the addition of a beam splitter 52 which separates the returning light in the microscope head and focuses it through a lens 54 onto an end of a second optical fibre 53 via which it is transmitted to the photodetector 34B of the system.

Figure 4:
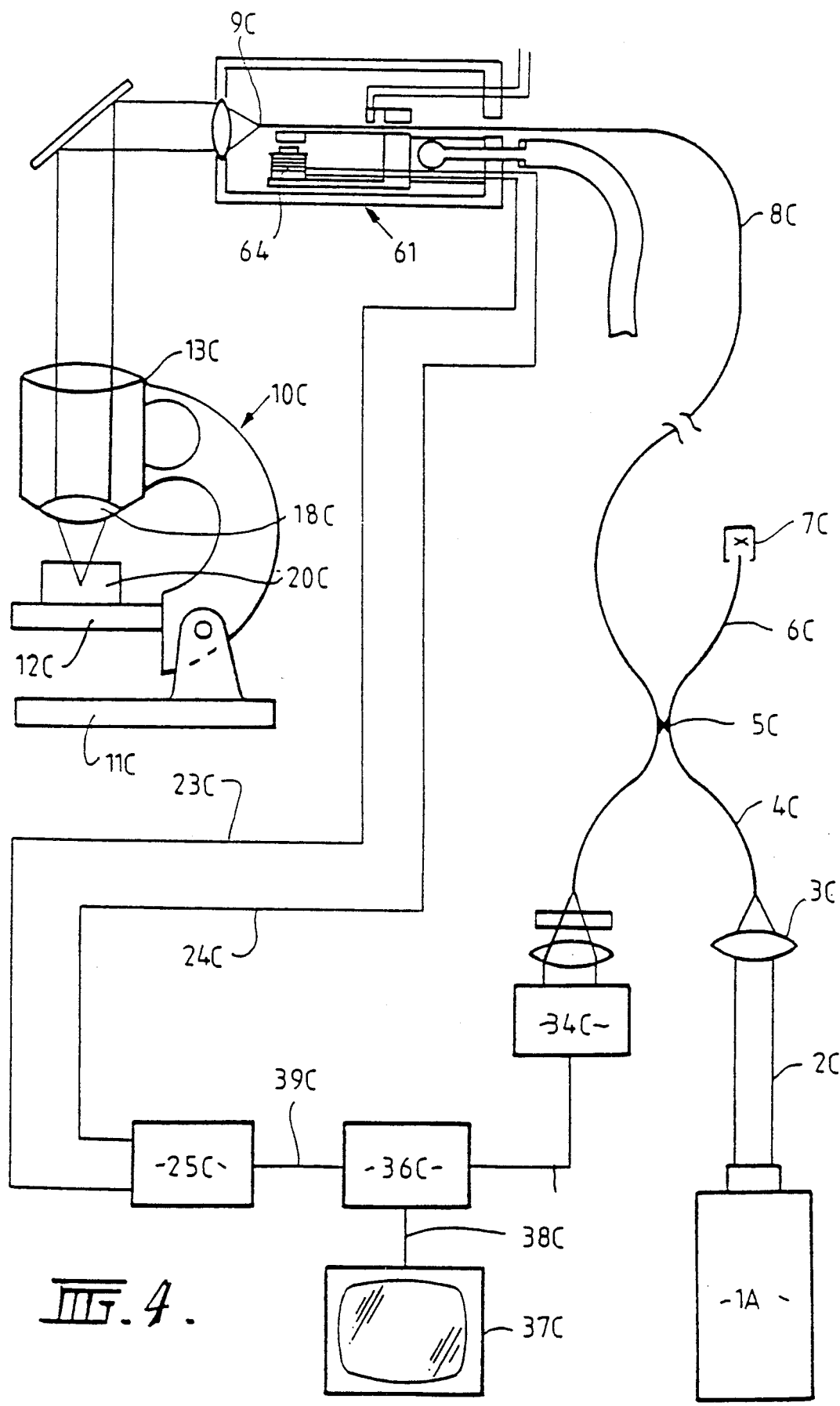
FIGS. 4, 5A and 5B illustrate an alternative confocal microscope system similar to that illustrated in FIG. 1 but in which scanning is achieved by movement of a tip of an optical fibre in the flexible optical transmitter means of the system.
Figure 5A:
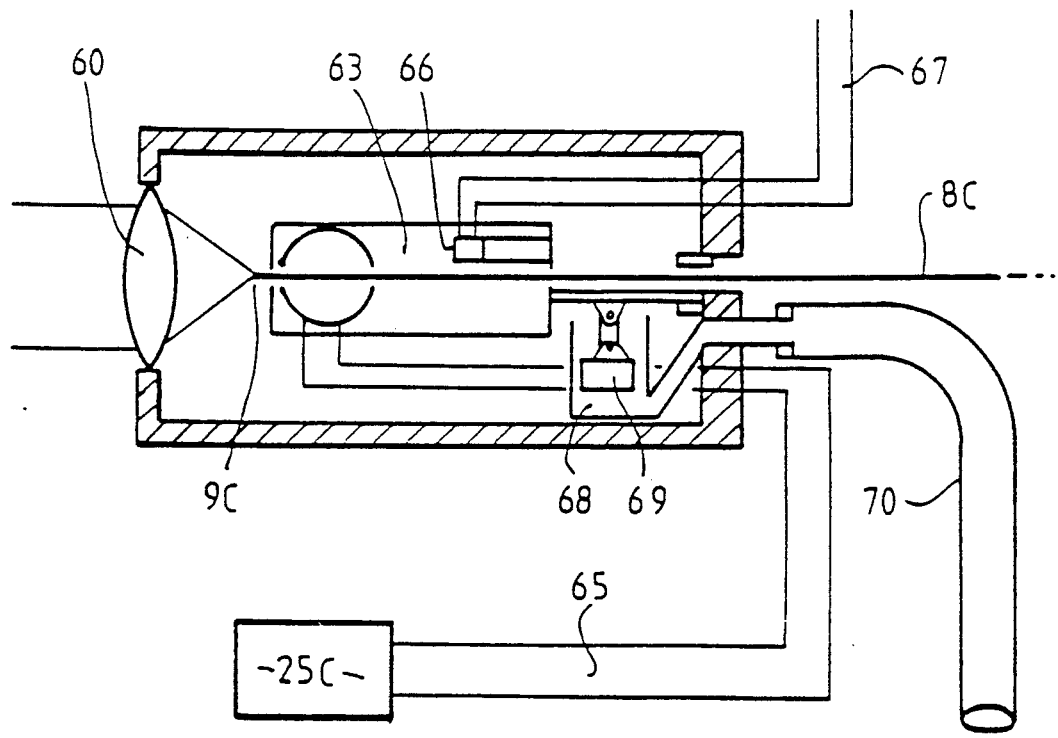
Figure 5B:
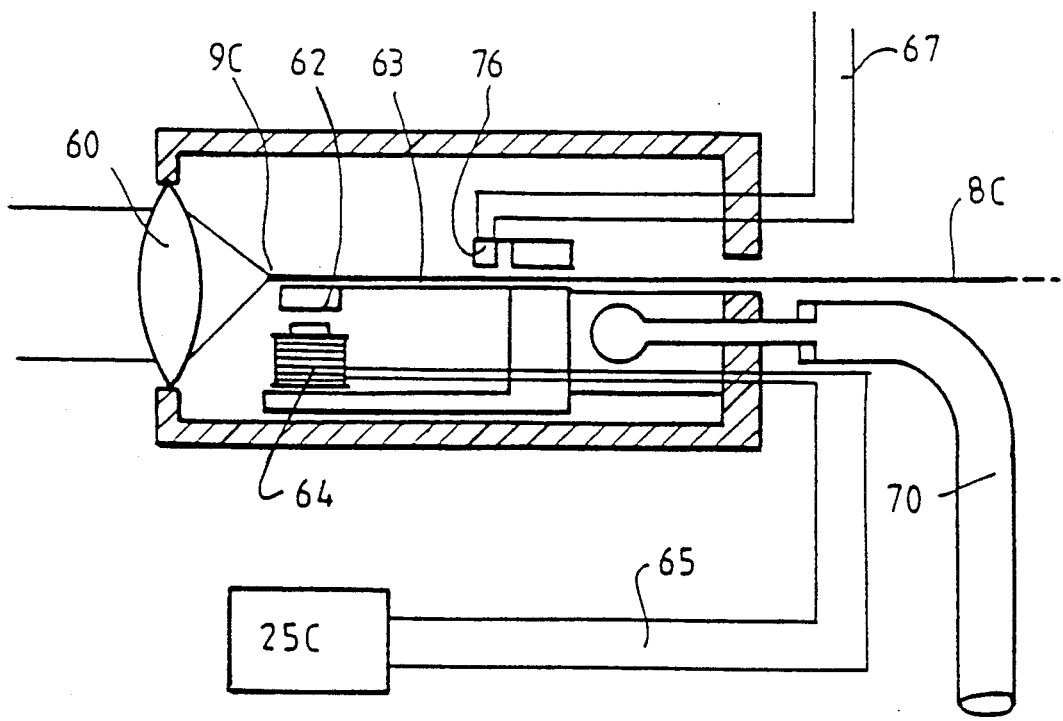

FIGS. 4, 5A and 5B illustrate a further modified scanning confocal microscope system constructed in accordance with the invention. This system is quite similar to that illustrated in FIG. 1 and like components have been identified by the same reference numerals with the addition of the post script C. The modification which has been made to the apparatus as previously described with reference to FIG. 1 is that scanning is now achieved by movement of the tip 9C of the optical fibre 8C through which light from the laser generator 1C is being transmitted to the microscope head 10C. Scanning movements of the fibre tip are generated by means of a movement generator 61. The movement generator may conveniently be an electro-mechanical transducer which received electrical signals from the scanning pattern generator 25C. This transducer may be of any convenient kind for generating appropriate scanning movements in the X and Y directions. One such device is illustrated in FIGS. 5A and 5B which are side and top views of a typical device.

In the fibre movement generator 61 as illustrated in FIGS. 5A and 5B, the scanning movements of the fibre tip 9C are provided by a combination of electromagnetically induced resonant oscillation and hydraulic movement. A permanent magnet 62 attached to a flexible reed 63 is periodically attracted by the electromagnet 64 under the influence of electrical pulses generated by the scan control unit 25C and carried to the optic head by the leads 65.

The optic fibre 8C projects along the flexible reed and is vibrated by it thus generating the scan in one dimension (say the X direction). To ensure that the electronic image scanning is synchronized with the mechanical scanning, positional feedback is provided from a piezo electric sensor 66 feeding back via leads 67 to the image processing unit 36C.

The other scan axis movement is generated by a slower quasi-linear movement produced by the influx or efflux of liquid from a supply tube 70 into a cylinder 68 thus actuating a piston 69 which carries the entire electromagnetic scanning unit so that the fibre tip is thus moved in the Y direction.

It will be appreciated that in all of the embodiments of the invention thus far described, the light source, detector and display system may be located at any position remotely from the other components, such as the opto-mechanical components usually incorporated in an optical microscope. These systems therefore enable the production of laser imaging equipment which can be attached to existing conventional microscopes so as to use the standard microscope optics and mechanical adjustments. The possibility of separating the optical head from the remainder of the system making use of optical fibre connections also opens the possibility for miniaturisation of the optical head, particularly if scanning is achieved by fibre movements. It is thus possible to apply the invention to endoscopy and other fields where a compact and remote head is required.

Figure 7:
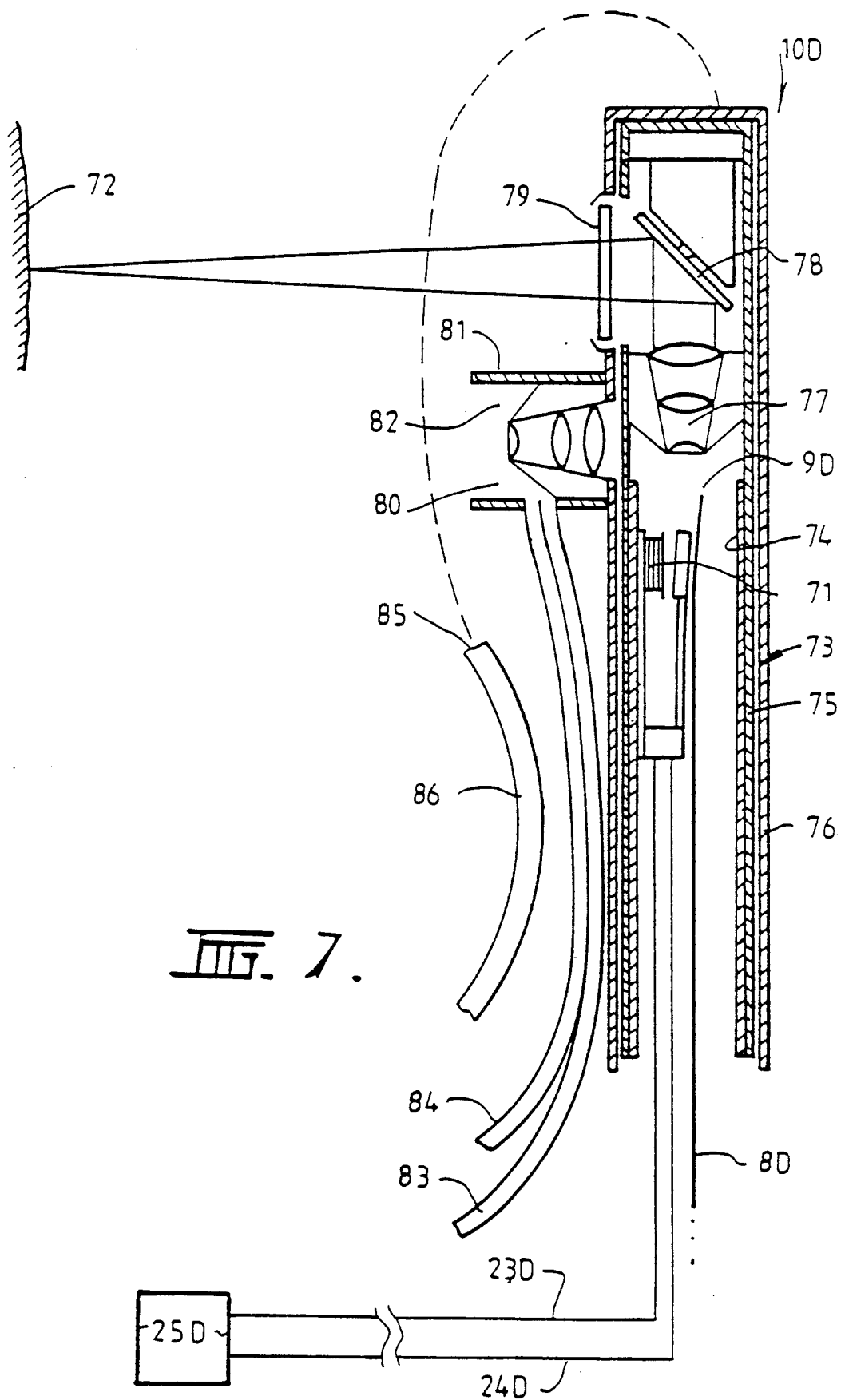
Figure 8:
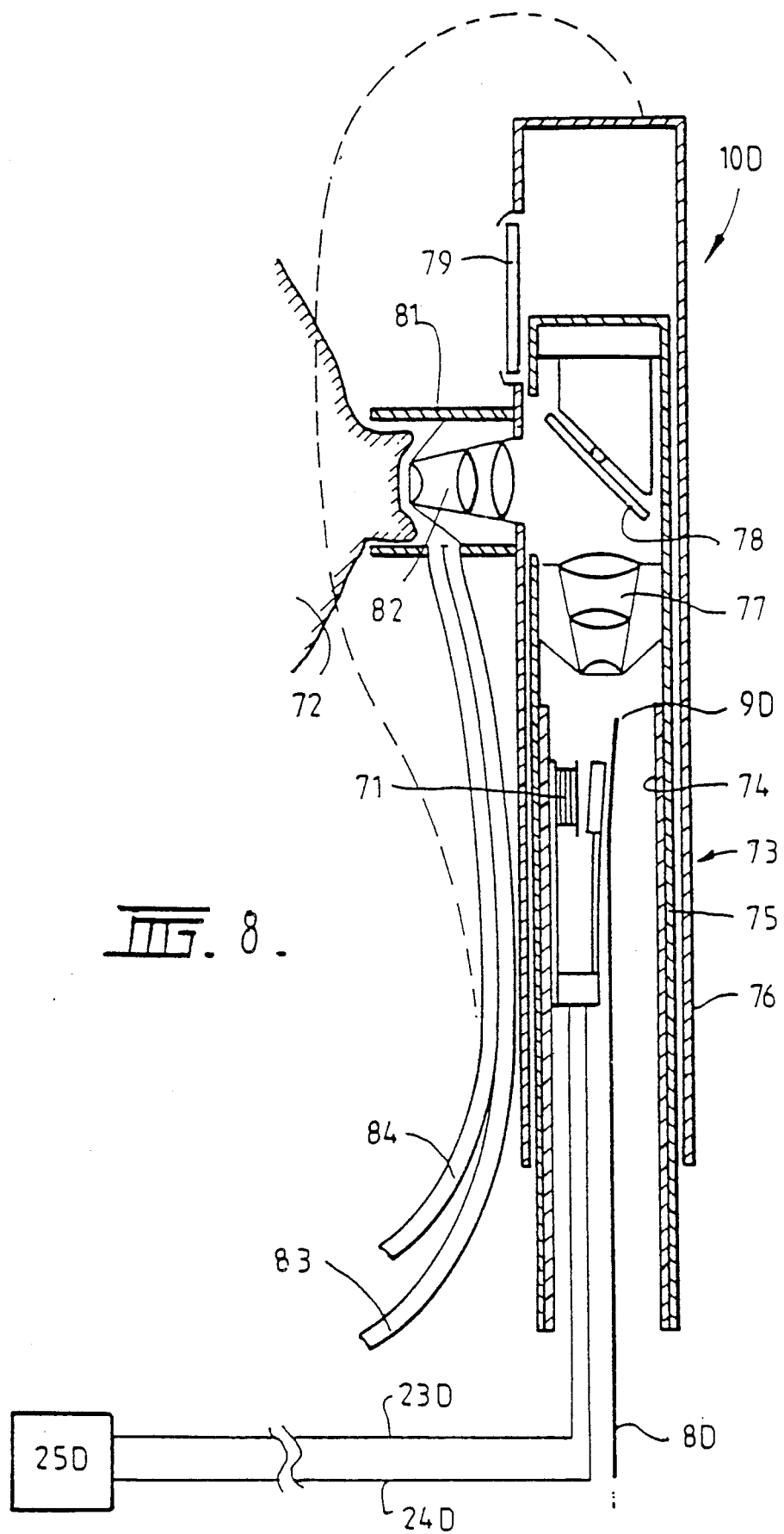

FIGS. 6 to 8 illustrate a system constructed in accordance with the invention which incorporates an endoscope head for examining soft tissue within body cavities. This system is generally based on that illustrated in FIG. 1 and like components have been identified by the same reference numerals with addition of the post script D. In this case, the microscope 10 of the system illustrated in FIG. 1 is replaced by an endoscope head 10D which is connected to the optical fibre 8D of the system. In this case, scanning is achieved by movement of the tip 9D of fibre 8D generated by an electro-mechanical transducer 71 located within the endoscope head and receiving signals from the scanning signal generator 25D via the connections 23D, 24D. Transducer 71 may be similar to the transducer 61 used in the previous embodiment and described with reference to FIG. 5.

Endoscope head 10D is designed so that it can be used to carry out a preliminary low power exploratory examination of a general area of soft tissue 72 before focusing in on one particular spot for high power examination. The endoscope head comprises an inner barrel 73 comprised of tubes 74, 75 and an outer barrel 76 slidable on the inner barrel between a retracted position as shown in FIG. 7 and the extended position shown in FIG. 8.

Inner barrel 73 houses a collimating lens system 77 to receive light transmitted from fibre 8D to produce a slightly convergent beam directed onto a mirror 78 mounted at the end of the inner barrel. When the outer barrel is in the retracted position shown in FIG. 7, this beam is reflected through a transparent port 79 in the barrel directly to the area of soft tissue 72 to be examined.

Barrel 76 has an outwardly projecting tubular spigot 1 which houses a focusing lens system 82. The spigot defines a cup 80 closed at its base by the lens system 82 and when the outer barrel is moved to its retracted position as illustrated in FIG. 8 the light beam from the collimating lens 77 is reflected by mirror 78 onto the focusing lens system 82. A pair of flexible tubes 83, 84 extend along the exterior of the endoscope head and communicate with the cup 80 through a port in the side of spigot 81. These tubes allow suction to be applied to the interior of the cup to suck soft tissue to be examined into the cup as illustrated in FIG. 8 and also to supply cleansing fluid to be supplied so as to bathe the area to be viewed to clear any obstructing debris from the optic path.

When the endoscope head 10D is first brought near the soft tissue area to be examined, the outer barrel is held in its extended position so that the focusing lens system 82 is held out of the optic path and the slightly converging beam from the collimating lens 77 is projected as a spot onto the soft tissue area as illustrated in FIG. 7. The spot is then scanned over a relatively large field area due to movements of the tip 9D of fibre 8D produced by the movement generator 71. When a particular spot is identified for closer examination, the outer barrel is moved to the extended position as illustrated in FIG. 8 to bring the focusing lens system 82 into the optic path and the tissue to be examined is sucked into the end of spigot 81 by application of suction to one of the tubes 83 so that it is properly positioned and held steady for high power confocal microscopic examination. Cleansing liquid may be applied through the other tube 83 to cleanse the area to be examined and then sucked out through the vacuum tube.

When the endoscope head is in the condition of FIG. 7 for imaging a relatively large field area of a distant object the confocal return of the system may be poor. In that event, light to provide modulation of the raster image may be picked up by the tip 85 of an incoherent fibre bundle 86 extended along the endoscope head and running back to the photo-detector. With the system in this mode it is also possible to obtain a view of the distant field object without use of the laser. To do this, high intensity light may be conveyed by the incoherent optic fibre bundle to the tip so as to illuminate the object. The scanning fibre tip 9D then picks up light as it rasters through the image space and carries it back to the photo-detector so that an image is built up from the photo detector output signal. Alternatively, the object could be illuminated directly by an incandescent globe placed at the outer end of the endoscope head.

Figure 9:
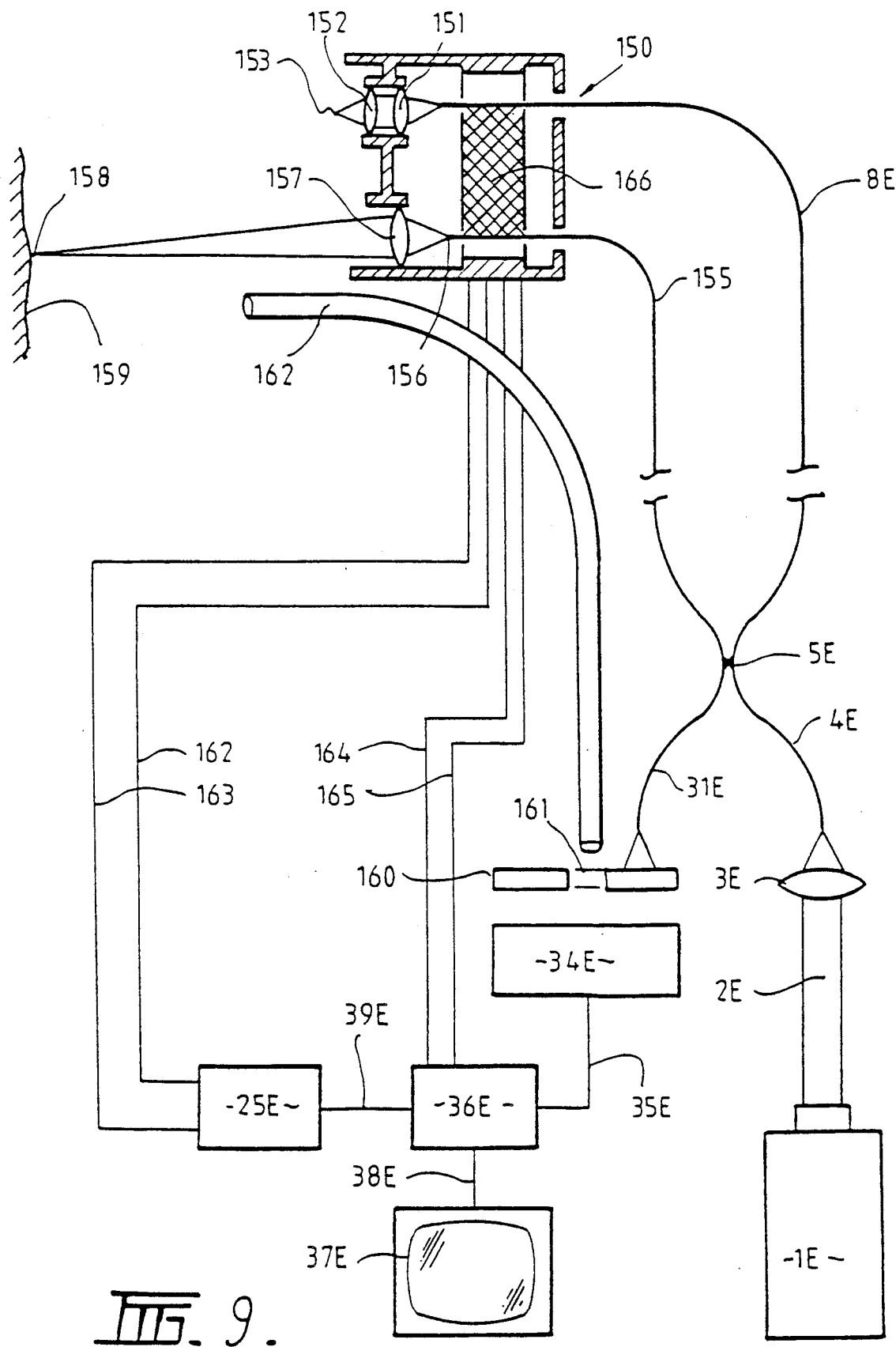
FIG. 9 illustrates a further system similar to that of FIGS. 6 to 8 but employing a modified endoscope head.

FIG. 9 illustrates an alternative system which will allow the viewing of distant objects and also allow high power confocal observation. Components equivalent to those of the system illustrated in FIG. 1 have been identified by the same reference numerals with the addition of the post script E. In this system Fibre 8E leads to an optical head 150 whereby it passes through a collimating lens 151 and condensing lens 152 to allow observations of objects positioned at the point observational field 153 by means of light confocally returned through the optic system the photodetector 34E. Fibre 155 which in previous descriptions has been labelled as fibre 6 has been terminated in a non absorbing medium in this embodiment led to a tip 156 which is held on the same movement generation head as is fibre 8E. This allows the two fibre tips to be scanned synchronously by the movement actuation system 166.

The light emanating from tip 156 of fibre 155 is focussed by a separate lens 157 to a distant spot 158 which scans over the object to be viewed 159. Some of the light emanating from the scanned spot 158 enters the end of a fibre optic bundle 162 and is carried back to the photo-detector 34E. Selection of which method of viewing is to be chosen is achieved by means of a plate 160 containing an aperture 161 which can be moved so that it allows either the light from fibre 31E or the end of the fibre optic bundle 159 to fall on the photo-detector.

Scanning actuation signals are carried by leads 162 and 163 and positional feedback signals by leads 164 and 165.

Figure 10:
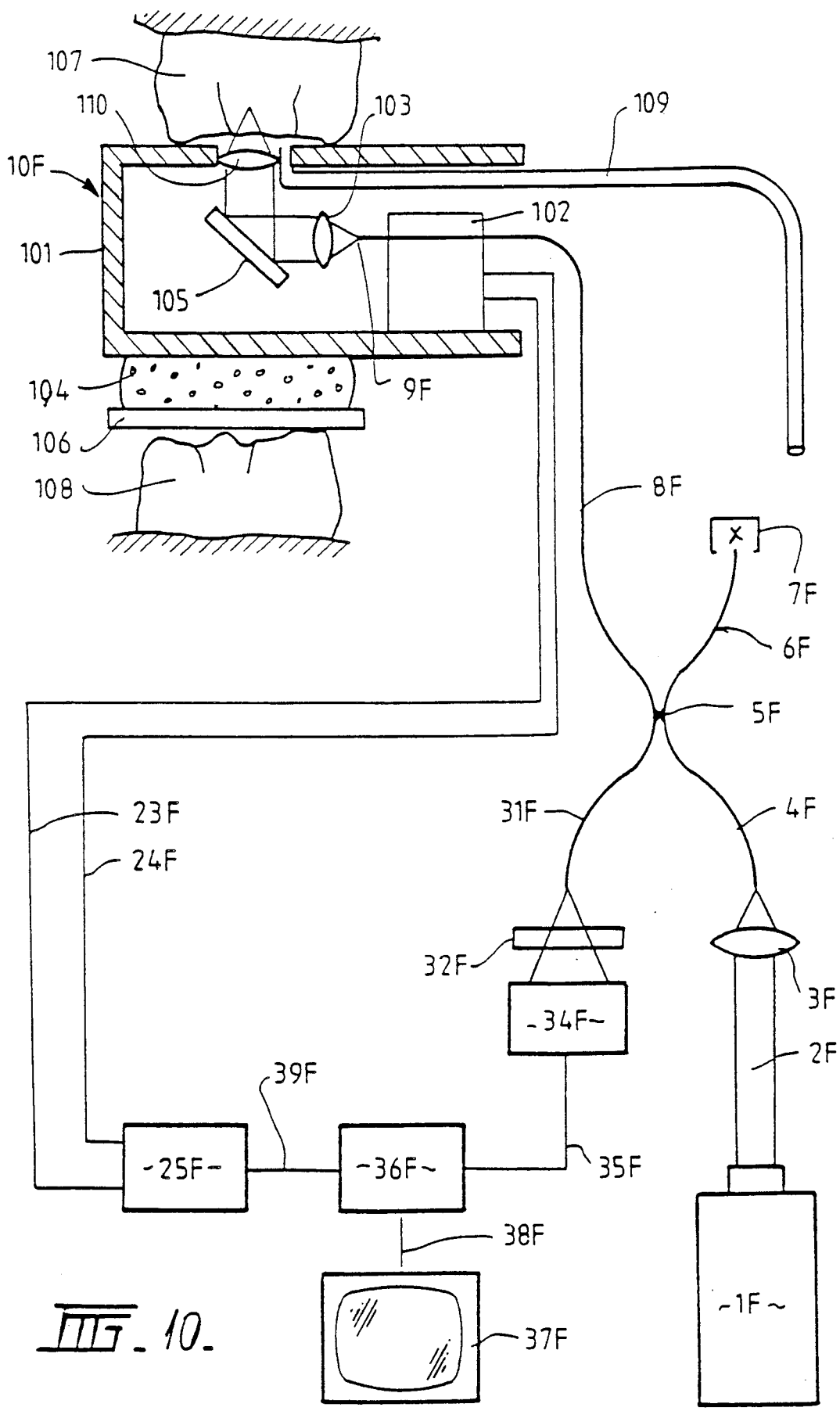
FIG. 10 illustrates a further modified system using a compact optic head designed particularly for the examination of teeth.

FIG. 10 illustrates a further modified system constructed in accordance with the invention in which components corresponding to those of the system illustrated in FIG. 1 are identified by the same reference numerals with addition of the post script F. In this case, the microscope head 10 is replaced by a compact optic head 10F for the examination of teeth, particularly for the detection of early caries pockets in the dentine below the enamel. The optic head 10F comprises a rigid housing 101 which receives the end of optical fibre 8F, the tip 9F of which is moved by an electro-mechanical transducer 102 to produce the required scan. Housing 101 contains the condenser lens 103 of the system and a lens 110 and mirror 105 to provide the optic path between the fibre 8E and the condenser lens 103.

A "sandwich" layer 104 of spongy or soft flexible material is adhered to the side of housing 101 opposite to the condenser lens 103 and this is covered by a relatively hard plate 106.

Optic head 10F is gripped between a tooth 107 to be examined and an opposite tooth 108 so that the tooth to be examined is disposed over the condenser lens 103 and the opposite tooth grips the plate 106. Sandwich layer 104 allows some relative movement between the teeth without causing movement between the optical head and the tooth being scanned. A tube 109 may be provided to introduce index matching gel or viscous fluid into the space between the objective lens and the tooth being examined.

Figure 11:
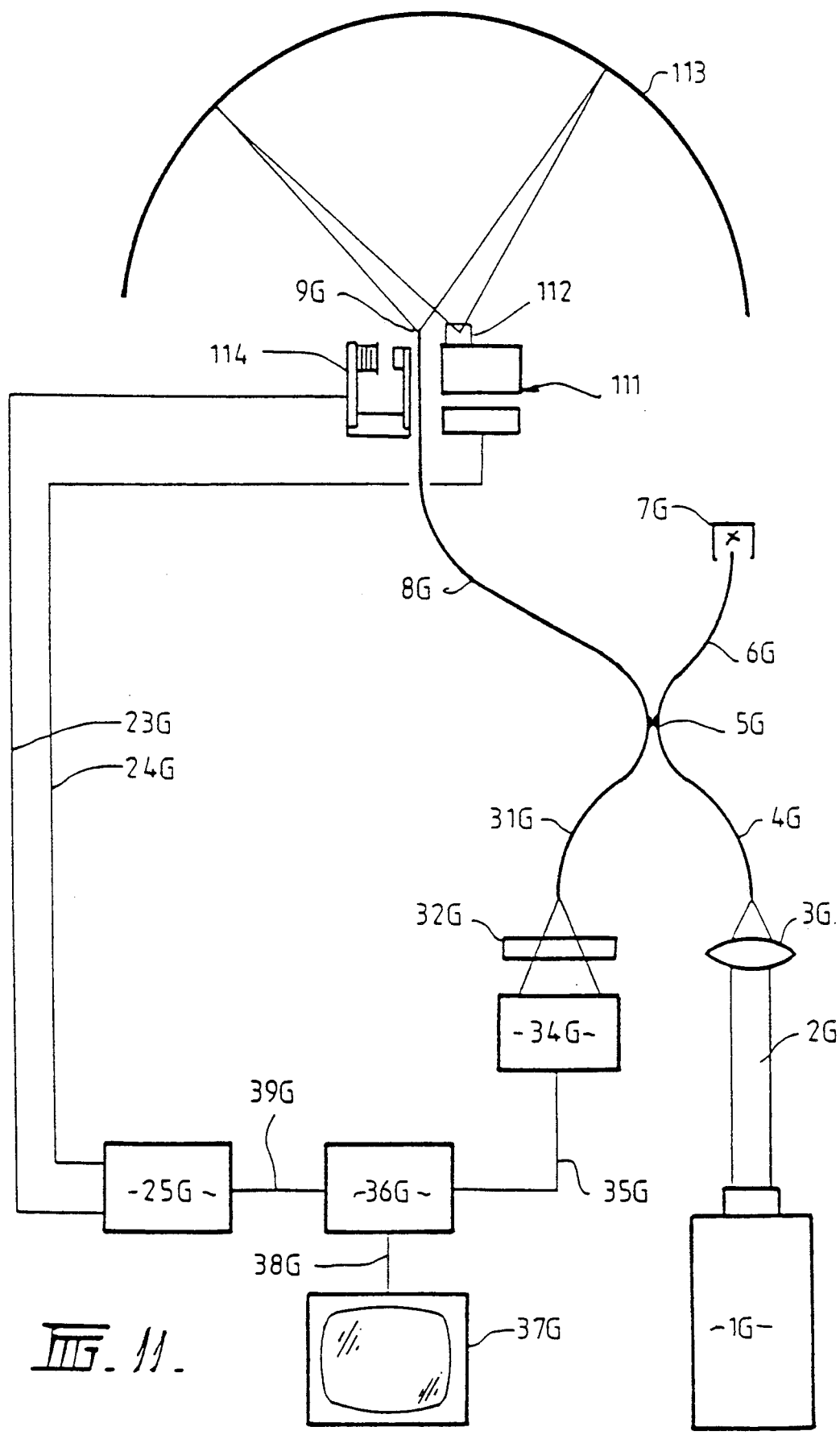
FIG. 11 illustrates a confocal system which uses a concave spherical mirror as the light condenser rather than a lens system.

FIG. 11 illustrates a further confocal microscope system constructed in accordance with the invention. This system uses a concave spherical mirror as the light condenser rather than a lens system. Components of the system corresponding to those of FIG. 1 have been identified by the same reference numerals with the post script G.

In the system illustrated in FIG. 11 the tip 9G of the optical fibre 8G is located close to a table 111 to support a specimen 112 to be examined. The fibre tip and the table are disposed close to and on opposite sides of the centre of curvature of a concave spherical mirror 113. The light emitted from the fibre tip is returned by the mirror to a focus on the specimen. Light emanating from the specimen due to reflection or fluorescence then returns confocally back to the fibre tip and hence to the photo-detector 34G.

An electro-magnetictransducer 114 is attached to the fibre tip and receives signals from the scanning signal generator 25G to cause scanning movements of the fibre tip. It will be appreciated that scanning might alternatively be achieved by movement of the specimen support table 115 or by a combination of movements of both the specimen support table and the fibre tip.

The system illustrated in FIG. 11 will not suffer from chromatic aberration. Spherical aberration will be small if the fibre tip and the specimen are located close to one another. It is possible to compensate for any spherical aberration by a very slight mechanical distortion of the spherical mirror surface into an ellipsoid of revolution having two focii coinciding with the fibre tip and the spot on the specimen under examination. Such distortion may be induced by mechanical clamping or other means. It would also be possible to put a small cylindrical element close to the fibre tip to introduce astigmatism in the opposite direction and thus reconvert the image to a spot for the outgoing and returning beams.

Figure 12:
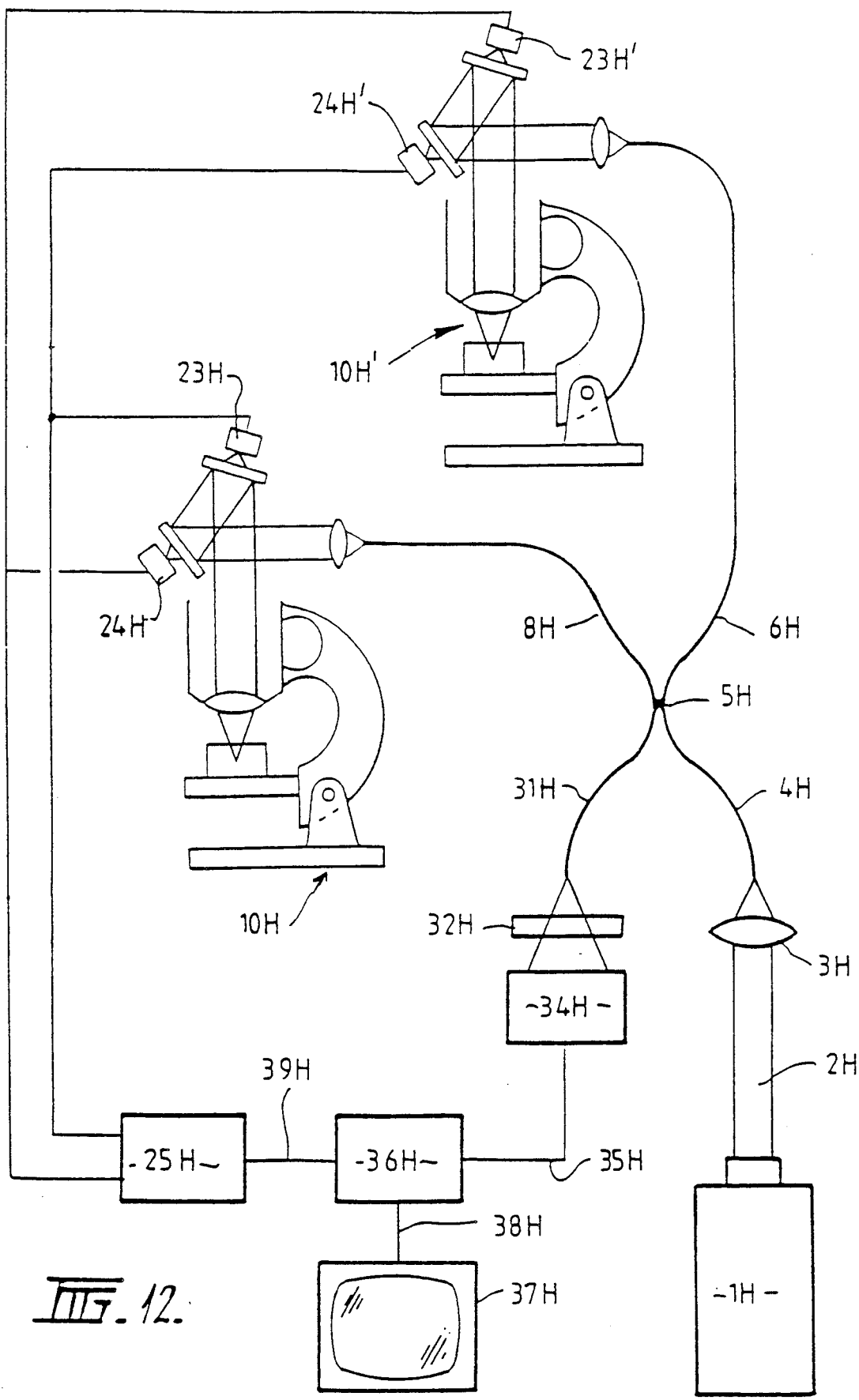
FIG. 12 illustrates a confocal system with two microscope heads.

FIG. 12 illustrates a confocal system which enables use of the microscope heads in alternation. The system is a modification of the system illustrated in FIG. 1 and the components equivalent to those in the system of FIG. 1 are designated by the same reference numerals with the addition of the post script H. In this case the limb 6H of the coupler 5H is not blanked off by connection to an absorber body but is connected by a fibre 121 to a second microscope head 10H' which may be identical to the first microscope head 10H and also has its scanning mirror transducers 23H' and 24H' connected to the scanning signal generator 25H.

With the arrangement shown in FIG. 12 one microscope head can be set up and focused onto a specimen while the other is being used for confocal viewing and can then be brought in the operation for confocal viewing as soon as viewing with the other head has been completed. In this way the system can be maintained in virtually continuous operation.

The illustrated embodiments of the invention have been advanced by way of example only and they could be modified and developed further to take advantage of optical fibre technology. For example, although in all of the illustrated embodiments single optical fibres are used for transmission of the light beam, it will be appreciated that multiple fibres may be used. In that case, the tips of the fibres which receive the returning object emanated light to produce a confocal image may be staggered slightly longitudinally of the fibre (i.e. in the direction of light travel) to enable the depth of the viewing field to be increased. Where scanning is achieved by fibre movement the whole bundle of fibres may be attached to the transducer or other fibre movement generator so as to be moved together. Where scanning is achieved by other means such as moving mirrors or by moving the specimen, the staggered fibre tips may be fixed in place relative to the light condenser. Use of multiple fibres will also enable simultaneous scanning at differing wavelengths.

In another modification the optical coupler in FIG. 1 could be transversely cleaved at its midpoint so as to produce an end or tip from which light is transmitted to the microscope head and on which object emanated light is focused to produce the confocal image. Fibre 8 would then be eliminated and the end of the cleaved coupler would take the place of the fibre end or tip 9.

In a further modification the cleaved coupler could have three convergent limbs with the additional limb supplying light from a laser source of a different wavelength to enable multiple wavelength scanning.

INDUSTRIAL APPLICATION

The invention has particular application to scanning confocal microscopes for laboratory use and to confocal microscope systems which have compact remote heads suitable for use in endoscopic or other examination of living biological tissue.

I claim:

1. A scanning confocal epi-illumination microscope comprising:
    a light source for supply of a light beam;
    a light condenser for condensing light from said beam onto an object to illuminate a point observational field on or within the object and for receiving light emanating from that point obserational field on or within the object;
    a detector for detecting object emanated light received by the light condenser;
    optical transmission means for transmitting the light beam from the light source to the condenser and for transmitting the object emanated light received by the light condenser to the detector; and
    scanning means operable to cause relative movement between the object and the point observational field such that the point observational field traverses the object in a scanning pattern;
    said optical transmission means comprising flexible single mode optical transmitter means for transmitting the light beam between the light source and the condenser and a light separator means for separating the object emanated light from the light beam for application to said detector.

2. A microscope as claimed in claim 1, wherein the scanning means comprises means to move the light beam transmitted by the transmission means to the condenser to produce said relative movement between the object and the point observational field.

3. A microscope as claimed in claim 2, wherein the scanning means comprises means to move a part of the flexible optical transmitter means to move the light beam transmitted to the condenser whereby to produce said relative movement between the object and the point observational field.

4. A microscope as claimed in claim 3, wherein the scanning means comprises an electro-mechanical transducer attached to said part of the flexible optical transmitter means so as to move it in response to electrical signals produced by a scanning signal generator.

5. A microscope as claimed in any one of claims 1, 2, 3 or 4, wherein the flexible single mode optical transmitter means comprises a first optical fibre means extending from the light source to the light separator means and a second optical fibre means extending form the light separator means to the detector.

6. A microscope as claimed in claim 5, wherein the light separator means comprises an optical fibre coupler coupling said first and second fibre means to a third optical fibre means providing an optical path for transmission of the light beam from the light source to the condenser and transmission of object emanated light from the condenser to the coupler.

7. A microscope as claimed in claim 6, wherein the scanning means operates to move the light beam transmitted from the third optical fibre means to the condenser.

8. A microscope as claimed in claim 7, wherein the scanning means provides an optical path for the light beam from the third optical fibre means to the condenser and comprises means operable to cause shifts in that optical path whereby to cause the scanning movement of the light beam.

9. A microscope as claimed in claim 8, wherein the means operable to cause shifts in the said optical path comprises movable reflector means.

10. A microscope as claimed in claim 7, wherein the scanning means is operable to move the third optical fibre means so as to move the beam transmitted thereby to the condenser whereby to produce said scanning movement of the light beam.

11. A microscope as claimed in claim 1, wherein the flexible single mode optical transmitter means comprises a first optical fibre means extending from the light source to the light separator means and a second optical fibre means extending from the light separator means to the detector, the light separator means comprises an optical fibre coupler coupling said first and second fibre means to a third optical fibre means providing an optical path for transmission of the light beam from the light source to the condenser and transmission of the object emanated light from the condenser to the coupler, and the scanning means comprises an electro-mechanical transducer attached to said third fibre means so as to move an end of that fibre means from which light is transmitted to the condenser in response to electrical signals produced by a scanning signal generator.

12. A microscope as claimed in any one of claims 1, 2, 3 or 4 wherein the light separator means comprises a beam splitter disposed between the light source and the flexible optical transmitter means.

13. A microscope as claimed in claim 5, wherein the light separator means comprises a beam splitter disposed between the condenser and said first and second optical fibre means.

14. A microscope as claimed in claim 2, wherein the flexible single mode optical transmitter means comprises an optical fibre means for transmitting the light beam from the light source to the light condenser and for transmitting the object emanated light from the condenser to the light separator, the scanning means comprises fibre moving means to move said fibre means so as to move the beam transmitted thereby to the condenser whereby to produce the scanning movements of the light beam, and said fibre means extends to a microscope head having a body housing the light condenser and said fibre moving means.

15. A microscope as claimed in claim 14, wherein said fibre moving means is an electro-mechanical transducer attached to an end of the fibre means within said microscope head.

16. A microscope as claimed in claim 1 wherein the light condenser is mounted on a body defining a cup for application to an object to the examined and there is means to apply suction to the cup whereby the microscope is adapted to examination of soft tissue which can be drawn into the cup by suction and thereby held in a steady position relative to the light condenser.

17. A microscope as claimed in claim 16, further comprising means to introduce fluid into the cup to cleanse the object to be examined.

18. A microscope as claimed in claim 1 wherein the condenser comprises a first condensing means to condense the light beam into a convergent form and a second condensing means to further condense the light beam into a second more convergent form and wherein the second condensing means is movable to an inoperative position to enable the microscope to scan an object at a distance over a relatively large field area and produce an image from object emanated light captured by the first condensing means and then to an operative position to enable higher magnification scanning of the object at a closer distance and over a relatively small field area.

19. A microscope as claimed in claim 18, including an optical fibre transmitter to receive light directly from said object when being examined with the second condensing means in its inoperative position and to transmit that light to the detector for modulation of said image.

20. A microscope as claimed in claim 18 or claim 19, comprising means for direct illumination of said object when being examined with the second condensing means in its inoperative position.

21. A microscope as claimed in claim 1, wherein the flexible single mode optical transmitter means comprises an optical fibre means for transmitting the light beam from the light source to the light condenser and for transmitting the object emanated light from the condenser to the light separator and the condenser comprises a concave reflector disposed about a tip of the optical fibre so as to focus light transmitted from the fibre tip at a point near to the fibre tip, the microscope further comprising means to support an object to be examined so as to be illuminated by the light focused by the mirror and so that objected emanated light is focused by the reflector onto the fibre tip.

22. A microscope as claimed in claim 1 wherein the light source is one of a pair of light sources for supply of a pair of beams of light of differing wavelengths and the optical transmission means is effective to combine those beams for transmission to the condenser to cause illumination of said point observational field with light at said differing wavelengths.

* * * * *